United States Patent
Stradella

[19]

[11] Patent Number: 6,082,356
[45] Date of Patent: Jul. 4, 2000

[54] DEVICE FOR PRE-DOSING OF A POWDERY PRODUCT FOR A PRODUCT DISPENSER

[75] Inventor: Giuseppe Stradella, Camogli, Italy

[73] Assignee: Tebro, Luxembourg

[21] Appl. No.: 09/029,762

[22] PCT Filed: Sep. 3, 1996

[86] PCT No.: PCT/EP96/03849

§ 371 Date: Sep. 18, 1998

§ 102(e) Date: Sep. 18, 1998

[87] PCT Pub. No.: WO97/09082

PCT Pub. Date: Mar. 13, 1997

[30] Foreign Application Priority Data

Sep. 4, 1995 [FR] France .................................. 95 10344

[51] Int. Cl.[7] ........................ A61M 15/00; A61M 16/00; B05D 7/14; B65D 83/06
[52] U.S. Cl. ............................... 128/203.15; 128/203.12; 604/58
[58] Field of Search ........................ 128/200.14, 200.17, 128/203.12, 203.15, 203.23; 604/58; 206/467–471, 528, 531, 532, 538

[56] References Cited

U.S. PATENT DOCUMENTS

| 5,207,217 | 5/1993 | Cocozza et al. ................... 128/203.21 |
| 5,337,740 | 8/1994 | Armstrong et al. ............... 128/203.12 |
| 5,388,572 | 2/1995 | Mulhauser et al. ................ 128/203.15 |
| 5,437,270 | 8/1995 | Braithwaite ........................ 128/203.15 |
| 5,467,873 | 11/1995 | Kastenhofer ............................ 206/363 |
| 5,492,112 | 2/1996 | Mecikalski et al. ............... 128/203.15 |
| 5,622,166 | 4/1997 | Eisele et al. ........................ 128/203.12 |
| 5,673,793 | 10/1997 | Seidler ..................................... 206/531 |
| 5,709,202 | 1/1998 | Lloyd et al. ........................ 128/200.14 |
| 5,778,873 | 7/1998 | Braithwaite ........................ 128/203.15 |
| 5,785,049 | 7/1998 | Smith et al. ........................ 128/203.15 |
| 5,794,781 | 8/1998 | Roulin et al. ............................ 206/531 |
| 5,924,417 | 7/1999 | Braithwaite ........................ 128/203.15 |

FOREIGN PATENT DOCUMENTS

| 469 814 | 2/1992 | European Pat. Off. . |
| 44 00 083 | 7/1995 | Germany . |
| 44 00 084 | 7/1995 | Germany . |
| 2 270 293 | 3/1994 | United Kingdom . |
| WO 93/16748 | 9/1993 | WIPO . |

Primary Examiner—John G. Weiss
Assistant Examiner—Joseph F. Weiss, Jr.
Attorney, Agent, or Firm—Sughrue, Mion, Zinn, Macpeak & Seas, PLLC

[57] ABSTRACT

A device (2) for pre-dosing a powder for a dispenser that includes an expulsion channel (12), the device being characterized in that it comprises at least one hermetically closed reservoir (4) each containing a dose of powder that is to be expelled on each actuation of the dispenser, said dispenser including a transfer device (16, 17) designed to transfer an entire dose of powder from one of said at least one reservoir (4) towards said expulsion channel (12) on each actuation of the dispenser, said transfer device (16, 17), when actuated, exerting pressure on a portion of a reservoir (4), each reservoir (4) including a closure wall (6) adapted to open totally and in predetermined manner towards the outside of the reservoir under the effect of the pressure created by actuating said transfer device (16, 17). A transfer element such as an insert (1) may optionally be placed in each reservoir (4).

10 Claims, 5 Drawing Sheets

DEVICE FOR PRE-DOSING OF A POWDERY PRODUCT FOR A PRODUCT DISPENSER

The invention relates to a device for pre-dosing a powder for a dispenser, and more particularly for an inhaler.

The term "inhaler" is used to mean any inhaler device whether actuated manually or by the user inhaling, whether passive, i.e. whether the powder is expelled by the flow of air created by the user, or active, i.e. where the flow of air is created by the device. The invention applies particularly to dry powder inhalers.

In the field of dry powder inhalers, there exist two main families of powder dispenser device in common use:

devices of the type having a multi-dose reservoir, in which the powder is contained in a single common reservoir, the device being provided with appropriate measuring means to ensure that it dispenses a determined quantity of powder on each actuation; and devices of the pre-dosing type in which each dose of powder is contained in a separate cavity that is hermetically sealed.

At present, pre-dosing type devices are particularly advantageous for powders having molecules that are fragile, e.g. made up of long chains that are easily broken during handling, and that require a high degree of stability. This can be obtained only with the powder being genuinely kept separate from the atmosphere, as is typical for separately pre-dosed single-dose packaging.

In this application, packaging devices commonly referred to as "blister" packs have been found to be particularly suitable. By its very configuration, comprising a support provided with a plurality of separate dose-containing "blisters" or cavities that are hermetically sealed, e.g. by means of aluminum foil, a blister pack makes it possible to ensure that each dose is genuinely hermetically separate from the others.

Nevertheless, at present, the use of a blister pack is presently limited by numerous problems that arise in use.

One of the main drawbacks is due to the fact that to make a dose available for inhaling, it is necessary to use an inhaler which is provided with a device that is capable of opening the packaging (peeling, puncturing, or tearing the aluminum) in a manner that is effective.

At present, the following solutions are in use for obtaining this result:

The inhaler includes peeling means capable of peeling off the layer that closes each dose cavity. One such device is described, for example, in document FR-2 660 550. Nevertheless, that type of peeling device is very complicated to manufacture and assemble and is therefore very expensive.

The inhaler is provided with a needle which is used to pierce the aluminum immediately before the dose is dispensed. That solution suffers from the drawback of opening part only of the cavity that contains the powder, and also of folding aluminum back into the dose cavity. This means that portions of the dose remain trapped by the aluminum foil and consequently cannot be expelled in full by the flow of air produced by the user or by the inhaler while inhaling is taking place. This makes it very difficult to guarantee effective dose reproducibility, since it often happens that the dose is not dispensed in full.

The inhaler is provided with means somewhat similar to a small finger used for pressing against the plastic side of the blister cavity so as to create sufficient pressure inside the cavity to burst the aluminum foil and thus move the powder into the expulsion channel. That solution also suffers from a drawback. The pressure exerted on the powder, acting against the resistance provided by the aluminum foil before it breaks, causes significant compression to occur within the powder, thereby tending to agglomerate the powder into large lumps.

In document DE-44 00 083, a blister pack device is disclosed in which the cavities are provided with piercing means enabling powder compression to be reduced. Those piercing means act inside the cavity and pierce the membrane outwards. Nevertheless, that device also suffers from the aluminum membrane being opened in a manner that is partial or irregular and, in certain cases, provision is even made to detach said membrane completely from the cavity. In certain blister pack applications that is not a drawback, however it is incompatible and even dangerous in inhaler devices where a dose of powder is initially transferred from a blister into an expulsion chamber prior to being inhaled. In addition to the above-mentioned drawback of incomplete dose reproducibility, irregularly torn portions of the membrane or portions that have been torn off also run the risk of reducing or even blocking the flow of air required for expelling the powder, and even run the risk of being ejected and therefore inhaled together with the powder, with manifest harmful consequences.

An object of the present invention is to provide a device for pre-dosing a powder in an inhaler that avoids the above-mentioned drawbacks.

Another object of the present invention is to provide such a device in which all of the dose enclosed in an individual pack is dispensed into the expulsion channel of the inhaler.

Another object of the invention is to provide such a device in which no compression and/or compacting of the powder occurs as it passes from the individual reservoir towards the expulsion channel.

Another object of the invention is to provide a device in which an individual reservoir is opened in predetermined manner without any portion of said reservoir being capable of becoming detached, thereby avoiding any obstacle to expulsion of the powder and any danger of portions of said reservoir being inhaled.

The present invention thus provides a device for pre-dosing a powder for a dispenser that includes an expulsion channel, the device being characterized in that it comprises at least one hermetically closed reservoir each containing a dose of powder that is to be expelled on each actuation of the dispenser, said dispenser including a transfer device designed to transfer an entire dose of powder from one of said at least one reservoir towards said expulsion channel on each actuation of the dispenser, said transfer device, when actuated, exerting pressure on a portion of a reservoir, each reservoir including a closure wall adapted to open totally and in predetermined manner towards the outside of the reservoir under the effect of the pressure created by actuating said transfer device.

Preferably, at least one reservoir comprises a cavity defined by a top surface and a bottom surface, one of said surfaces being said closure wall and being suitable for opening outwards under the effect of pressure exerted on the other of said surfaces by said transfer device, said pressure being transmitted from one of said surfaces to the other via a substantially rigid hollow transfer element interconnecting said surfaces so that no pressure is exerted on the powder contained in said reservoir.

Advantageously, at least one reservoir comprises a shell having a top surface, said shell including an opening opposite said top surface that is hermetically closed by a tearable closure wall such as an aluminum foil, said wall being adapted to tear under the effect of a minimum pressure being exerted thereon, said transfer device, when actuated, exerting said minimum pressure on said top surface of the shell, said pressure being transmitted by said transfer element to said closure wall.

Advantageously, said transfer device comprises a pushbutton provided with a finger adapted to press on one surface of a reservoir on each actuation, thrust on the pushbutton causing said finger to exert pressure on said reservoir, said pressure being transmitted to said closure wall by said transfer element, said transfer element thus causing said closure wall to open and transferring all of the dose of powder towards the expulsion channel of the dispenser.

In a first embodiment of the invention, said transfer element is made in the form of at least one rigid insert disposed inside each reservoir.

In an advantageous variant embodiment of the invention, said insert is hollow and open in structure, the outside dimensions and shape of the insert being such that the insert is in contact with the middle of the closure wall along the entire length thereof, and such that the maximum section of the insert corresponds approximately to the surface of said closure wall. Advantageously, the insert can thus be put into place in the reservoir after it has been filled with the dose of powder.

Advantageously, said insert comprises parallel rings interconnected by longitudinal segments.

In an advantageous variant embodiment of the invention, the insert is a helical spring.

In yet another advantageous variant embodiment of the invention, the insert is in the form of a hollow rigid tube adapted to contain the dose of powder intended for each of the reservoirs.

The reservoirs may be disposed in any appropriate manner on any form of support, e.g. radially on a rigid or flexible disk, or parallel to one another on a strip, preferably a flexible strip.

Other characteristics and advantages of the invention appear from the following detailed description given by way of non-limiting example and with reference to the accompanying drawings, in which.

Figure 1A:
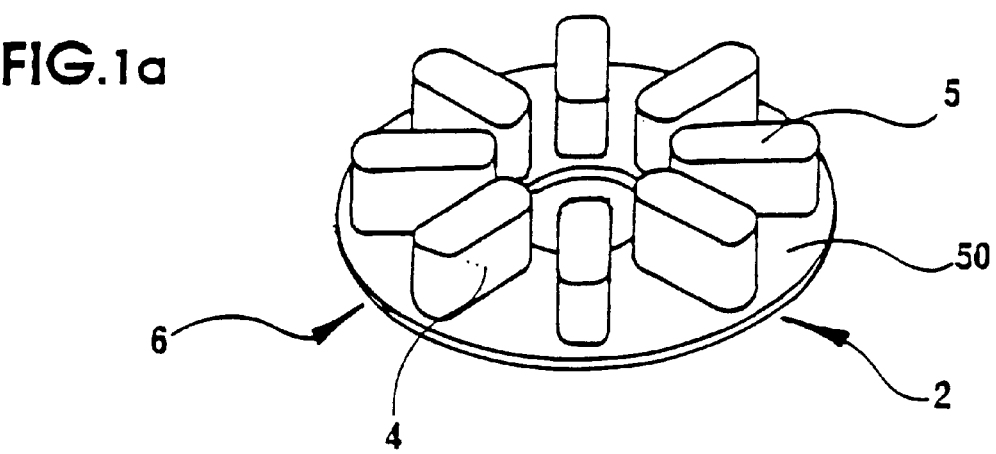
FIGS. 1a and 1b are diagrammatic views, respectively in perspective and in vertical section, of a pre-dosing device of the invention.
Figure 1B:
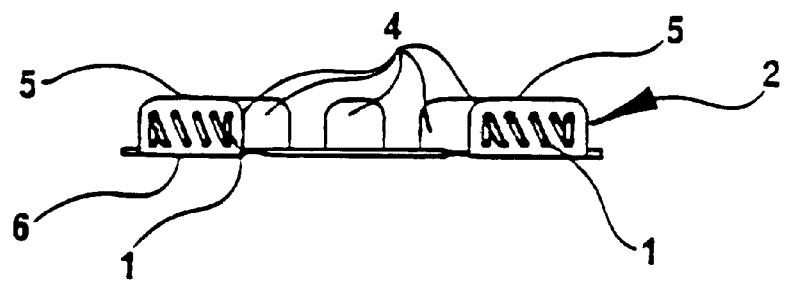
Figure 1C:
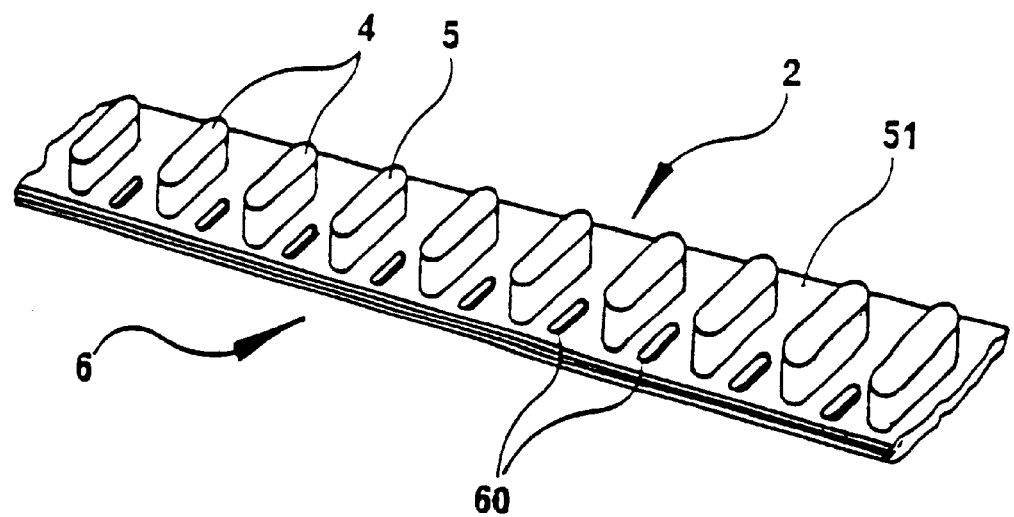
FIG. 1c is a diagrammatic perspective view of another implementation of the pre-dosing device of the invention.

With reference to FIGS. 1a and 1b, there can be seen an example of packaging 2, commonly referred to as being of the "blister" type, comprising eight individual reservoirs 4 advantageously constituted by a shell, e.g. of plastic or of aluminum, and each containing a measured quantity or "dose" of powder. The eight reservoirs 4 are hermetically closed by a closure wall 6 which is preferably in the form of an aluminum foil on the underside of the package 2. Naturally, the blister pack could be of any shape other than that shown in FIGS. 1a and 1b where it is substantially circular with the reservoirs being disposed substantially radially on a rigid disk 50 of said blister pack 2. The number of reservoirs 4 may be different, and instead of comprising a shell 5 covered on one side only by aluminum foil 6, the reservoirs could equally well be cavities that are open through two faces, closed respectively by top and bottom aluminum foils. Also, the reservoirs 4 of the blister pack 2 may be disposed parallel to one another on a strip 51, preferably a flexible strip, as shown in FIG. 1c.

Figure 10:
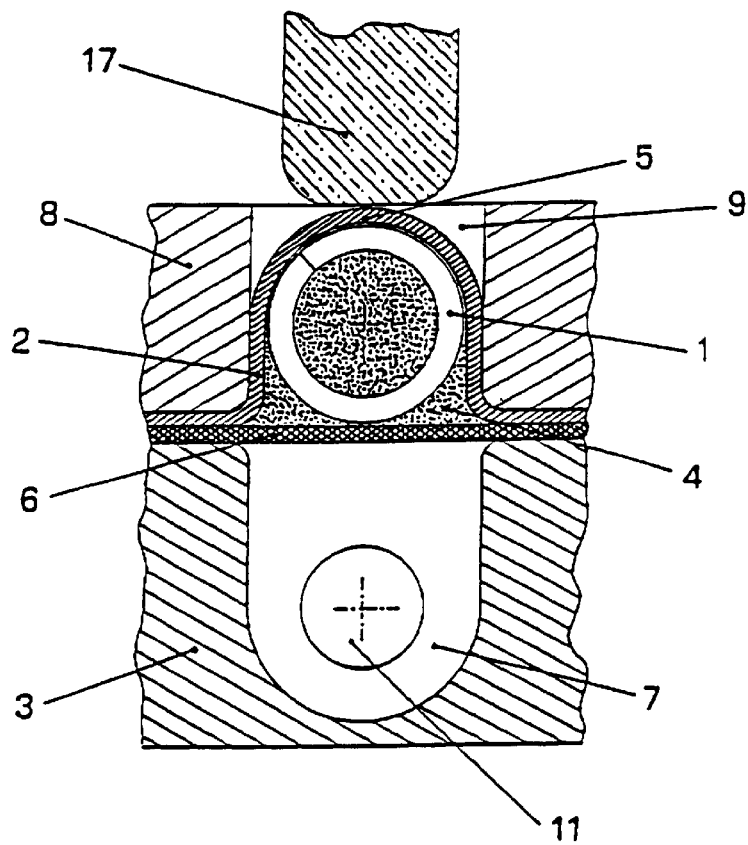
FIGS. 10 and 11 are diagrammatic vertical section views through a blister in an embodiment of the invention, respectively before and after transfer of powder into the expulsion chamber.

In an advantageous embodiment of the invention, provision is made to place at least one transfer element such as an insert inside each reservoir 4, said transfer element being substantially rigid and of a shape such that when said reservoir 4 is deformed, it comes simultaneously into contact with two opposite walls of the reservoir, in this example with the top wall of the plastic cavity 5 in the blister pack 2 and the aluminum foil 6 which closes said cavity. In this way, when pressure is exerted on the plastic shell of the blister pack in order to puncture or tear the aluminum foil, the pressure is transmitted directly through said rigid transfer element to the aluminum foil which is thus pierced by the transfer element without any pressure being exerted on the powder. Preferably, the transfer element is hollow and has outside dimensions that correspond substantially to the inside dimensions of the reservoir 4, such that while said reservoir 4 is being deformed, the transfer element comes simultaneously into contact with the opposite walls of said reservoir. In addition, the transfer element is of a shape such as to come into contact with the center of the closure wall 6 over its entire length, and such that its maximum section corresponds substantially to the surface area of said closure wall 6. This can be seen in FIGS. 10 and 11, in particular. The following advantageous results are thus obtained:

the initial pressure is transferred to a predetermined portion and over the entire length of the closure wall 6, thereby giving rise to controlled and predetermined opening (tearing) thereof, while ensuring after opening that there are neither any large portions of wall that could impede expulsion of the powder, nor any portions of wall that are completely detached from the reservoir and run the risk of being inhaled together with the powder; and opening of the closure wall is progressive and complete, providing the maximum section portion of the transfer element passes through the opening of the reservoir 4, and thus the entire dose of powder is transferred into the expulsion channel of the inhaler.

Figure 8:
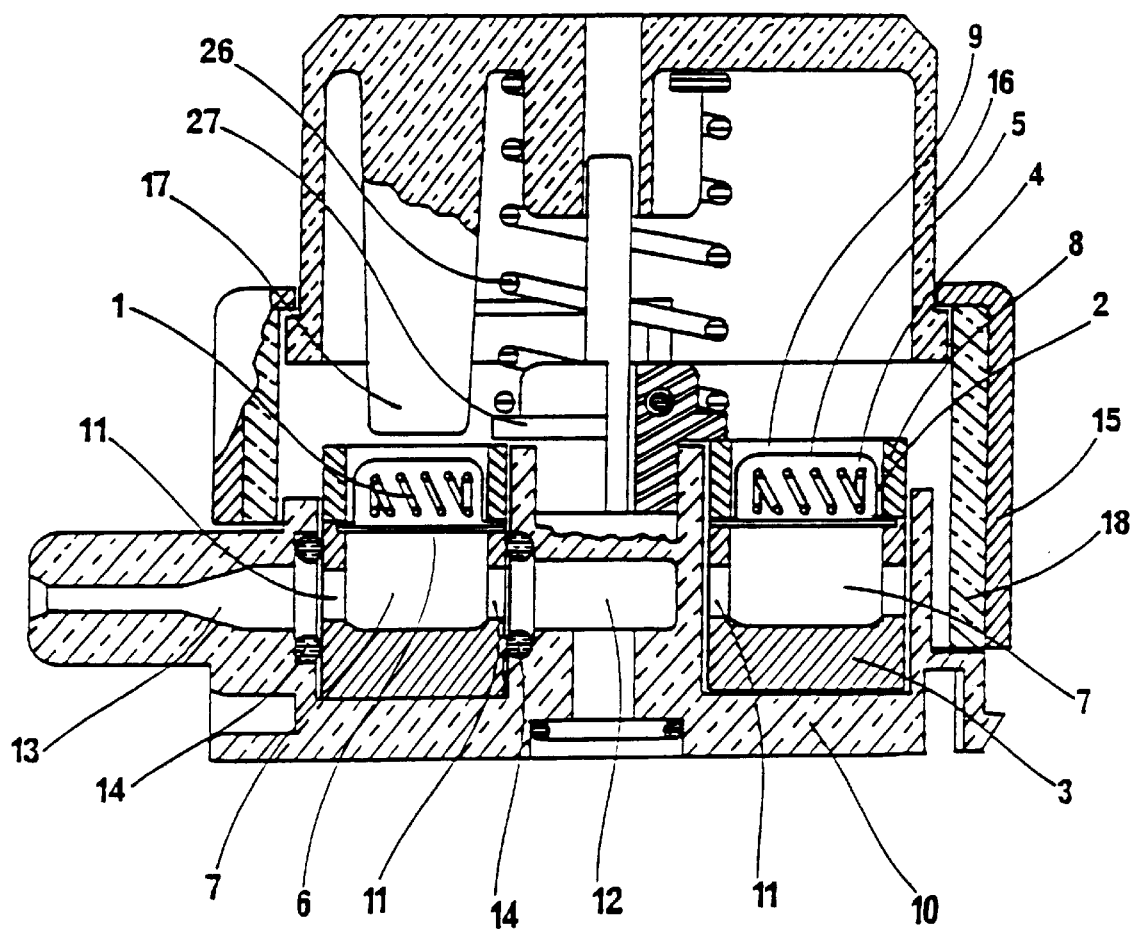
FIG. 8 shows one implementation of the predosing device of the invention in a particular example of an inhaler.
Figure 9:
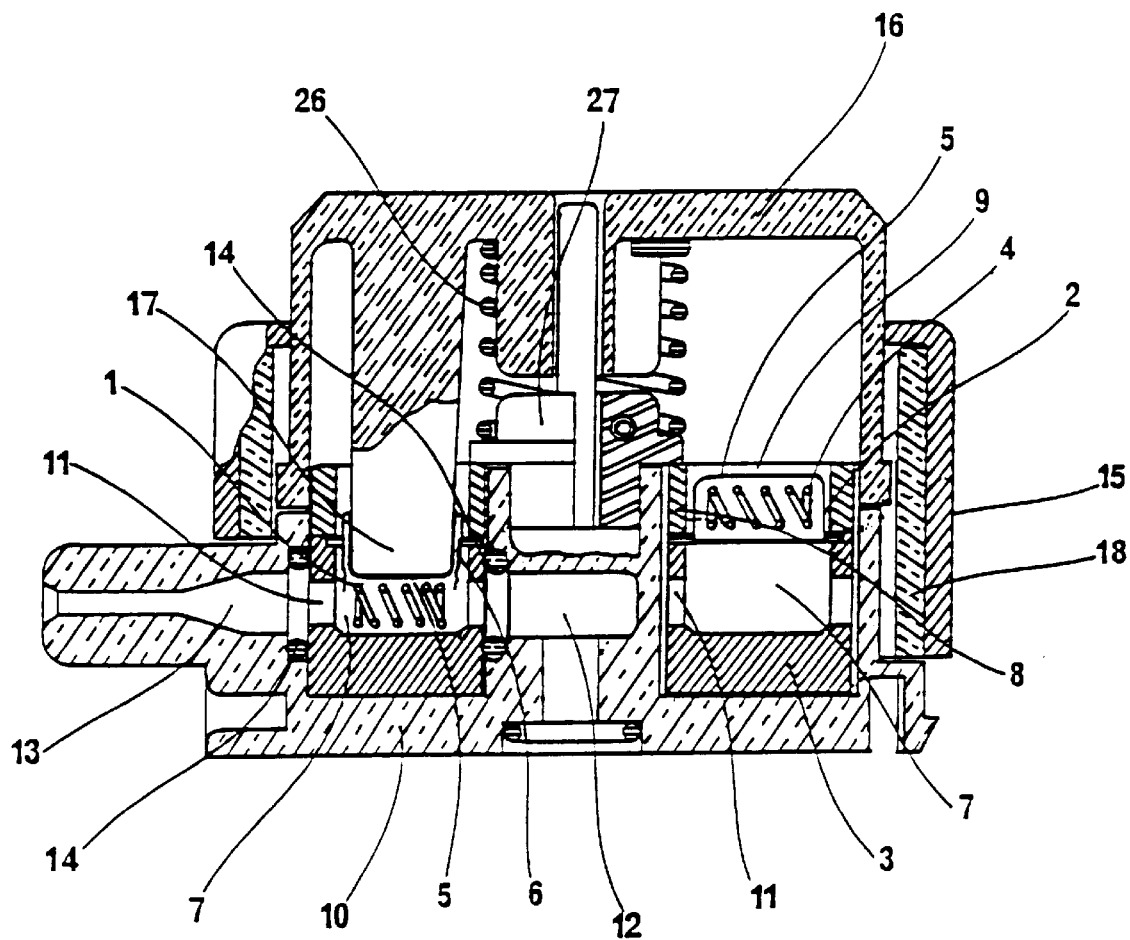
FIG. 9 is a view similar to FIG. 8 after the transfer device has been actuated.

As can be seen in FIGS. 1b and 2 to 7, the transfer element may be made in various different ways depending on the type of powder, the size of the dose, or the way in which the reservoir of the blister pack is filled. Thus, in FIG. 1b, the transfer element 1, referred to below as an "insert", is constituted merely by a helical element, e.g. a spring, which is disposed inside the reservoir 4. This is the embodiment of the insert which is also shown in FIGS. 8 and 9, to which reference is made below when describing an embodiment of the pre-dosing device of the invention in a particular inhaler.

Figure 2:
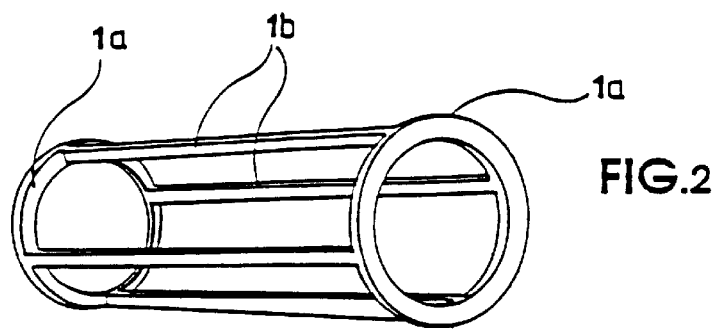
FIGS. 2 to 7 are diagrammatic perspective views of different variants of the insert of the invention.
Figure 3:
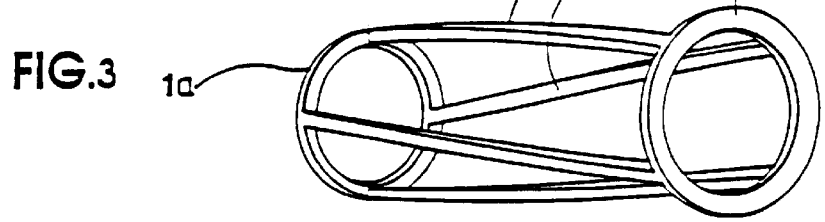
Figure 4:
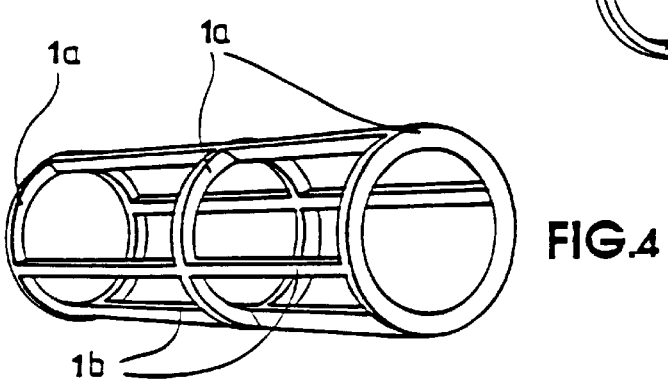

FIGS. 2 to 4 show three different inserts of substantially cylindrical shape, each being of open hollow structure with parallel rings 1a interconnected by longitudinal segments 1b. Thus the insert of FIG. 2 comprises parallel longitudinal segments 1b whereas the insert shown in FIG. 3 has longitudinal segments 1b that twist axially to form a helical structure. The insert of FIG. 4 is similar to that of FIG. 2 but it includes a central reinforcing ring 1a and it is used for larger measured quantities where a larger insert is required.

Because of their open segmented structures, all of the above-mentioned inserts (FIGS. 1b, 2, 3, and 4) can be placed in the reservoirs 4 of the blister pack after the reservoirs have been filled with powder. The inserts are of a structure that enables them to sink easily into the powder after it has been put into place in said reservoirs of the blister pack.

Figure 5:
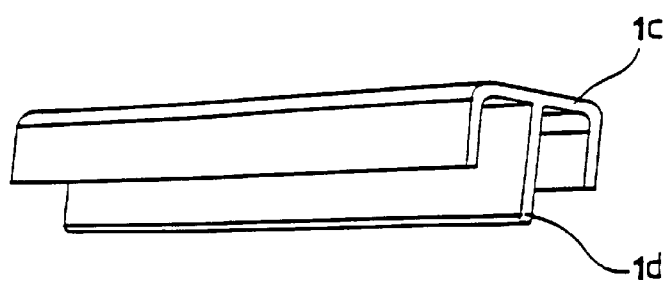

The insert shown in FIG. 5 has a solid base 1c of substantially rectangular section and is designed to be placed in the blister cavity before it is filled with powder. This insert has a central longitudinal rib 1d suitable for tearing the aluminum foil 6 in the center along its entire length, in the same manner as the above cylindrical inserts, thereby avoiding any excessively long aluminum margins after opening.

Figure 6:
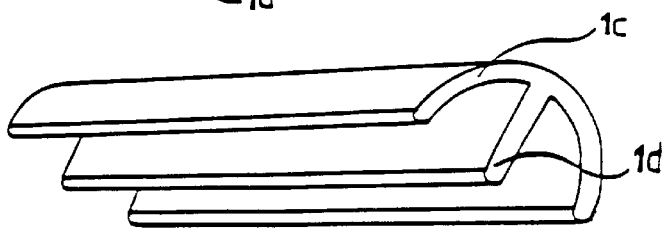

FIG. 6 shows an insert similar to FIG. 5, but using a base 1c of semicylindrical section.

Figure 7:

The insert shown in FIG. 7 is implemented merely in the form of a solid tube designed to be filled with powder before being inserted in the blister cavity.

The inserts shown in FIGS. 5 to 7 are thus designed to be put into a blister cavity before it is filled with powder, whereas the inserts shown in FIGS. 1b and 2 to 4 are designed to be put into place after the cavity has been filled with powder.

Naturally, all the above-mentioned configurations are merely examples and they can easily be combined with one another to form inserts of any other shape, e.g. having sections that are polygonal rather than cylindrical or rectangular. The main characteristic of inserts of the invention is that such an insert has outside dimensions and a shape such as to transmit all of the pressure exerted on one side of the reservoir directly to the other side, thereby enabling the closure wall 6 (advantageously an aluminum foil) to be broken or torn over its entire length with all of the powder in the reservoir being transferred to the expulsion channel of the inhaler without the powder being compressed.

Implementing a pre-dosing device of the invention in a particular inhaler is shown more completely in FIGS. 8 and 9. Naturally, the pre-dosing device of the invention is adaptable to any inhaler that includes such devices, and is not limited to the example shown in FIGS. 8 and 9 which are described below to explain operation thereof.

In the embodiment of the invention shown in FIGS. 8 and 9, the blister pack 2 is provided with cavities 4 each of which has a top surface 5, and an opening opposite said top surface 5 and hermetically closed by an aluminum foil 6, the blister pack 2 being disposed between a cylindrical body 3 and a cylindrical cover 8. The cover 8 is provided with openings 9 adapted to receive the blister cavities, and the body 3 is provided in corresponding manner with chambers 7 adapted to receive the inserts together with powder after said blister cavities are opened.

The chambers 7 are provided with holes 11 enabling a flow of air to pass through while powder is being dispensed to the user of the inhaler.

The body 3, the blister pack 2, and the cover 8 are advantageously assembled together in rigid manner to form a single unit. The unit is placed inside an appropriate cylindrical recess formed in a main body 10 of the inhaler in such a manner as to be rotatable relative to said main body 10. The main body 10 is provided with an air flow passage or "expulsion channel" 12 which passes through the chamber 7 via the holes 11 when the body 3 is put into a powder-dispensing position. The expulsion channel 12 then extends towards a mouthpiece 13 through which the powder is delivered to the user. When the chamber 7 is placed in its dispensing position, it is provided on either side with a respective sealing gasket 14 disposed around a respective hole 11, thereby preventing the flow of air becoming dispersed during inhaling, since that would reduce the effectiveness of the inhaler.

The main body 10 carries an external cover 15 fixed to said body 10 by appropriate means, said cover including a rotary pushbutton 16 that is axially displaceable. The pushbutton 16 includes a device for transferring powder to enable a dose of powder to be transferred from a blister cavity 4 into the expulsion channel 12 of the inhaler. This transfer device comprises a finger 17 of dimensions enabling it to penetrate into the openings 9 in the cover 8.

FIG. 8 shows the inhaler with the unit constituted by the body 3, the blister pack 2, and the cover 8 in position so that a chamber 7 is placed in the dispensing position, which means that its holes 11 are in register with the air flow passage (or inhaler expulsion channel) 12, and thus with the mouthpiece 13, via the sealing gaskets 14. FIG. 8 also shows the pushbutton 16 in an angular position such that the finger 17 is in a ready position which means that it is in register with the opening 9 in the cover 8 and thus facing the top surface 5 of a cavity 4 in the above-mentioned blister pack 2.

Figure 11:
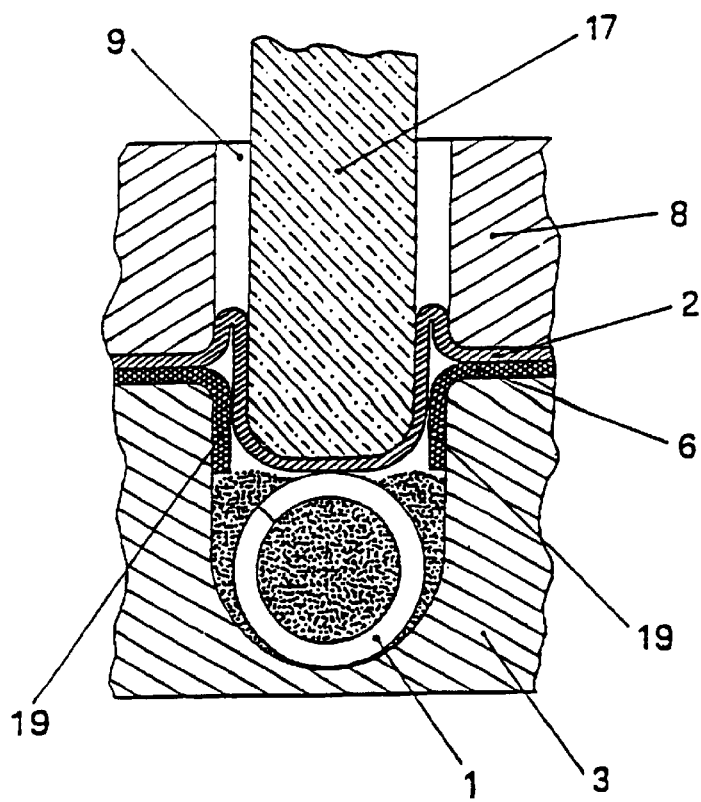

To open the blister and thus transfer the powder into the chamber 7, it suffices to press the pushbutton 16; this moves the pushbutton downwards and the finger 17 penetrates through the opening 9 in the cover 8 and presses down on the top surface 5 of the blister cavity 4 without breaking it. This movement is transferred directly by the insert 1 to the aluminum foil 6 which closes the cavity 4. When there is sufficient thrust, the aluminum foil 6 breaks or tears along the entire length of the insert. Advantageously, the aluminum foil, once torn, does not extend into the chamber 7 so as to avoid partially blocking the holes 11 which would spoil expulsion of the powder. To this end, the blister pack 2 is placed far enough above said chamber 7 and the aluminum foil 6 is torn in its center along its entire length, as explained above. Continued axial movement of the finger 17 moves the transfer element 1 through the opening of the blister cavity 4 and causes the closure wall 6 to open progressively and completely when the maximum section portion of the transfer element passes through said opening. In this way, torn marginal portions 19 of the wall 6 are formed that are of controlled and regular length, thereby enabling all of the powder to be transferred into the chamber 7 and enabling said powder to be expelled from said chamber 7 without obstacle, as can be seen in FIGS. 9 and 11. When the chamber 7 contains the insert 1 and the dose of powder, it can be emptied in any known manner by a flow of air, e.g. created by the user inhaling or by external means. This flow of air passes through the chamber 7 from the air passage 12 towards the mouthpiece 13 to dispense the dose of powder to the user. During this operation, the insert 1 remains in the chamber 7 since the diameter of the holes 11 is such as to prevent it being expelled.

After the dose has been expelled towards the user, the transfer device is returned to its ready position (FIG. 8) and the unit carrying the blister pack can be rotated through an appropriate angle to bring another cavity 4, chamber 7, and opening 9 into the dispensing position. To do this, the pushbutton 6 is advantageously provided with means that operate while it is rising under drive from a return spring 26 to rotate the unit comprising the body 3, the blister pack 2, and the cover 8 through the appropriate angle. The apparatus is then ready for further use.

Once all of the doses have been dispensed in the manner described above with reference to FIGS. 8 and 9, the unit comprising the body 3, the blister pack 2, and the cover 8 can be replaced with another unit.

Naturally, the inhaler described above is merely one example of an application of the pre-dosing device of the invention, this concept being suitable for use in various different ways, for example in an inhaler where only the blister pack 2 is replaced instead of a unit comprising the body 3, the blister pack 2, and the cover 8. Under such circumstances, the inhaler may have a single receptacle for collecting inserts after they have been transferred from a reservoir, said receptacle being emptied when the blister pack is replaced. Such an implementation is particularly adapted to blister packs containing a large number of reservoirs. Also, the dose of powder, after it has been transferred from its individual reservoir in the blister pack to the expulsion channel of the inhaler, can be expelled towards the user in any appropriate manner.

The transfer device may be different in shape, in particular when the blister pack is implemented in the form of a strip 51 (FIG. 1c). Thus, the finger may be replaced, for example, by a wheel which flattens the reservoirs on the strip one by one. The strip 51 may optionally include sprocket holes 60 enabling it to be driven by a sprocket wheel or any other appropriate device.

I claim:

1. A device (2) for pre-dosing a powder for a dispenser that includes an expulsion channel (12) and a transfer device (16, 17), said pre-dosing device comprising:

at least one hermetically closed reservoir (4) containing a dose of powder to be expelled upon an actuation of the dispenser, wherein on each actuation of the dispenser said transfer device transfers an entire dose of powder from one of said at least one reservoir (4) towards said expulsion channel (12) by exerting pressure on a portion of a reservoir (4), wherein each reservoir (4) includes a closure wall (6) adapted to open towards the outside of the reservoir due to the actuation of the dispenser, and wherein said at least one reservoir (4) comprises a cavity defined by a top surface and a bottom surface, one of said surfaces being said closure wall (6) which opens due to a pressure exerted on the other of said surfaces by said transfer device (16, 17), the pressure being transmitted from one of said surfaces to the other via a substantially rigid hollow transfer element (1) interconnecting said surfaces to prevent pressure from being exerted on the powder contained in said reservoir (4).

2. A device according to claim 1, in which said at least one reservoir comprises a shell having a top surface (5), and an opening opposite said top surface (5) being hermetically closed by a tearable closure wall (6), wherein said wall (6) tears with a minimum pressure being exerted thereon, and wherein said transfer device (16, 17) exerts said minimum pressure on said top surface (5) of the shell, and said pressure is transmitted by said transfer element (1) to said closure wall (6).

3. A device according to claim 1, in which said transfer device (16, 17) comprises a pushbutton (16) provided with a finger (17) adapted to press on one of said surfaces (5) of said at least one reservoir (4) on each actuation, wherein a thrust on the pushbutton (16) causes said finger (17) to exert pressure on said reservoir (4), said pressure being transmitted to said closure wall (6) by said transfer element (1), and said transfer element (1) causing said closure wall (6) to open and to transfer the dose of powder towards the expulsion channel (12) of the dispenser.

4. A device according to claim 1, in which said transfer element (1) is formed of at least one rigid insert (1) disposed inside each of said at least one reservoir (4).

5. A device according to claim 4, in which said insert (1) has a hollow and open structure, a length of the insert (1) being in contact with the middle of the closure wall (6), and a width of the insert (1) corresponding approximately to a width of said closure wall (6).

6. A device according to claim 4, in which said insert (1) comprises parallel rings (1*a*) interconnected by longitudinal segments (1*b*).

7. A device according to claim 4, in which the insert (1) is a helical spring.

8. A device according to claim 4, in which the insert (1) is a hollow rigid tube adapted to contain the dose of powder of said at least one reservoir (4).

9. A device according to claim 1, in which the reservoirs (4) are disposed radially on a rigid disk (50).

10. A device according to claim 1, in which the reservoirs (4) are disposed parallel to one another on a strip (51).

* * * * *